United States Patent
Faigle et al.

(10) Patent No.: US 11,054,492 B2
(45) Date of Patent: Jul. 6, 2021

(54) METHOD FOR SUPPORTING A USER WHEN POSITIONING AN ACCESSORY FOR A MAGNETIC RESONANCE EXAMINATION

(71) Applicant: Siemens Healthcare GmbH, Erlangen (DE)

(72) Inventors: Christine Faigle, Erlangen (DE); Bjoern Heismann, Erlangen (DE); Silke Quick, Essen (DE); Eva Rothgang, Schwaig bei Nuernberg (DE)

(73) Assignee: Siemens Healthcare GmbH, Erlangen (DE)

(*) Notice: Subject to any disclaimer, the term of this patent is extended or adjusted under 35 U.S.C. 154(b) by 381 days.

(21) Appl. No.: 16/028,674

(22) Filed: Jul. 6, 2018

(65) Prior Publication Data

US 2019/0008411 A1    Jan. 10, 2019

(30) Foreign Application Priority Data

Jul. 7, 2017 (EP) .................................. 17180288

(51) Int. Cl.

| | |
|---|---|
| *G01R 33/48* | (2006.01) |
| *A61B 5/055* | (2006.01) |
| *G01R 33/56* | (2006.01) |
| *G01R 33/34* | (2006.01) |
| *A61B 5/06* | (2006.01) |
| *A61B 5/00* | (2006.01) |
| *A61B 6/04* | (2006.01) |

(52) U.S. Cl.
CPC .............. *G01R 33/48* (2013.01); *A61B 5/055* (2013.01); *A61B 5/06* (2013.01); *G01R 33/56* (2013.01); *A61B 5/704* (2013.01); *A61B 5/706* (2013.01); *A61B 6/04* (2013.01); *G01R 33/34* (2013.01)

(58) Field of Classification Search
CPC ......... A61B 5/0555; A61B 5/055; A61B 5/06; A61B 5/70; A61B 5/704; A61B 5/706; A61B 6/04; A61B 6/0407; A61B 2034/2055; G01R 33/56; G01R 33/56375; G01R 33/56383
See application file for complete search history.

(56) References Cited

U.S. PATENT DOCUMENTS

| | | | |
|---|---|---|---|
| 8,587,293 B2 | 11/2013 | Biber et al. | |
| 2002/0120190 A1 | 8/2002 | Chang | |
| 2004/0081341 A1* | 4/2004 | Cherek | A61B 6/469 382/128 |
| 2005/0122108 A1 | 6/2005 | Yasuhara et al. | |

(Continued)

FOREIGN PATENT DOCUMENTS

KR    101525040 B1 *  6/2015

*Primary Examiner* — Carolyn A Pehlke
(74) *Attorney, Agent, or Firm* — Schiff Hardin LLP

(57) ABSTRACT

In a method and apparatus for supporting a user when positioning an accessory for a magnetic resonance examination on an examination object, the actual position of the accessory is acquired by an acquisition unit, and a target position of the accessory is determined by a determination unit. The actual position and the target position of the accessory are compared with regard to deviation of the actual position from the target position of the accessory. Output information representing any deviation that is found to exist is provided to a user via an output unit.

14 Claims, 2 Drawing Sheets

(56) References Cited

U.S. PATENT DOCUMENTS

| | | | |
|---|---|---|---|
| 2006/0164086 A1* | 7/2006 | Kohlmuller | A61B 5/0555 |
| | | | 324/307 |
| 2006/0264737 A1* | 11/2006 | Faber | A61B 5/055 |
| | | | 600/410 |
| 2009/0021257 A1 | 1/2009 | Yasuhara | |
| 2010/0156421 A1 | 6/2010 | Sukkau | |
| 2013/0181715 A1 | 7/2013 | Biber | |
| 2013/0279779 A1* | 10/2013 | Darrow | A61B 5/055 |
| | | | 382/131 |
| 2013/0342851 A1 | 12/2013 | Dresel et al. | |
| 2016/0007936 A1* | 1/2016 | Takahashi | A61B 5/7278 |
| | | | 600/407 |
| 2016/0202864 A1* | 7/2016 | Hardie | G01R 33/307 |
| | | | 715/771 |

* cited by examiner

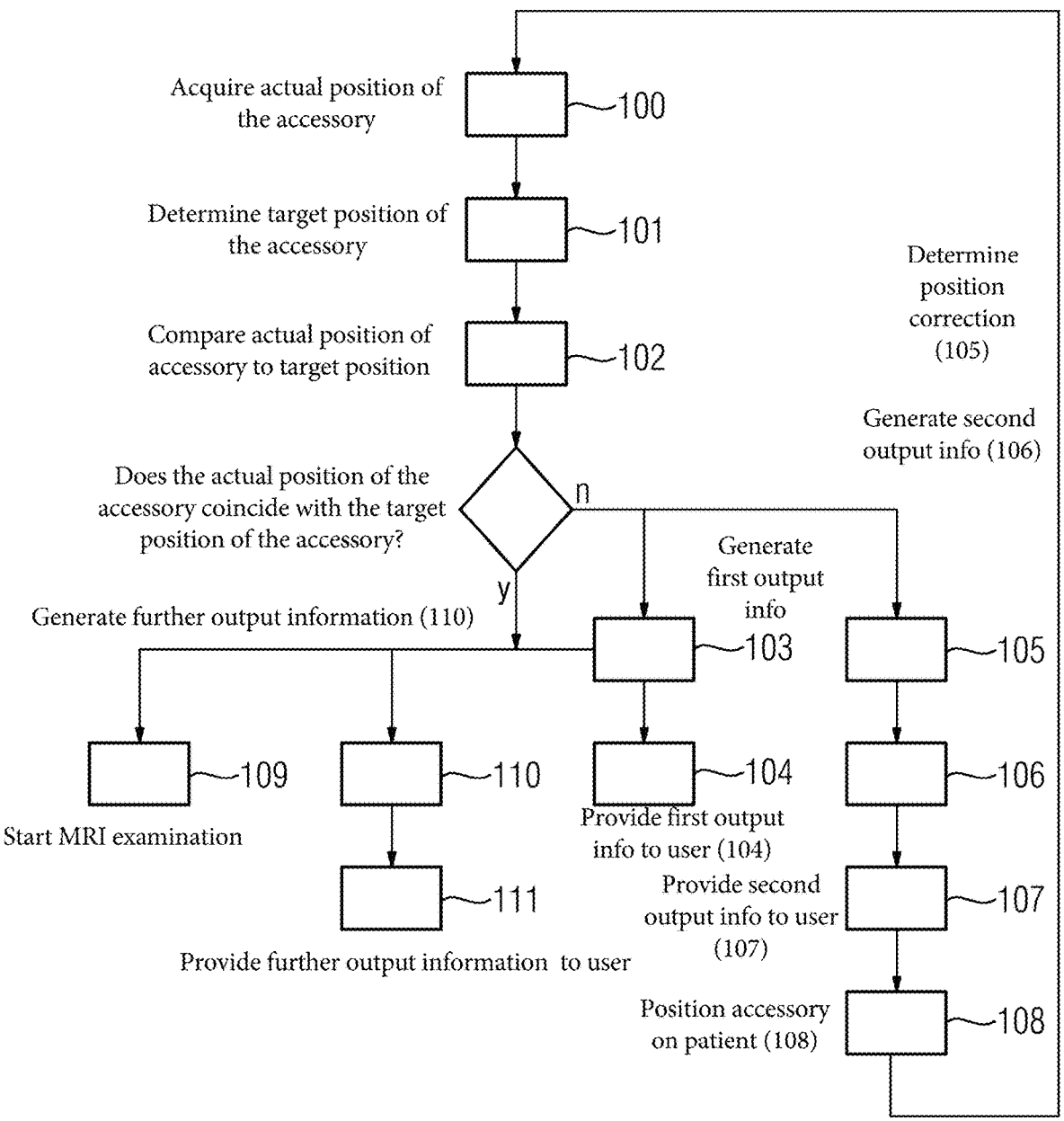

METHOD FOR SUPPORTING A USER WHEN POSITIONING AN ACCESSORY FOR A MAGNETIC RESONANCE EXAMINATION

BACKGROUND OF THE INVENTION

Field of the Invention

The present invention concerns a method for supporting a user when positioning an accessory for a magnetic resonance examination on an examination object. Furthermore, the present invention concerns a magnetic resonance apparatus designed to perform such a method as well as an electronically readable data storage medium for performing such a method.

Description of the Prior Art

For a magnetic resonance examination, accessory items such as local radio-frequency (RF) antennas, which are designed to receive magnetic resonance signals, should be located as close as possible to an examination object, for example surrounding the body area of the patient for examination. Radio-frequency antennas that are incorrectly positioned and/or arranged too far from the body area for examination may result in image artifacts in the acquired image data, or in a high signal-to-noise ratio. This may even result in the magnetic resonance examination having to be repeated in order to obtain useful and/or analyzable image data. Repetitions of magnetic resonance examinations are undesirable due to the additional stress for the patient and the increased amount of time that is spent.

In order to correctly position the local radio-frequency antenna required for a pending magnetic resonance examination on the appropriate body area of the patient for the examination, the user requires very good and extensive anatomical knowledge. Depending on the level of training of the user, such knowledge is often inadequate.

DE 10 2009 004 448 B4 describes a method for acquiring the positioning information of a radio-frequency antenna with regard to a magnetic resonance scanner. Furthermore, the recognition and determination of the position of local radio-frequency antenna by RFID is known from DE 10 2012 200 600 A1.

SUMMARY OF THE INVENTION

An object of the present invention is to support a user with the correct positioning of an accessory on an examination object for a magnetic resonance examination.

This object is achieved in accordance with the invention by a method for supporting a user when positioning an accessory for a magnetic resonance examination on an examination object that includes the following steps. The actual position of the accessory is determined by a position acquisition. A target position of the accessory is determined by a determination unit. The actual position of the accessory is compared in a computer with the target position of the accessory with respect to a deviation of the actual position of the accessory from the target position of the accessory. The processor generates output information from the comparison of the actual position with the target position of the accessory. The processor presents the output information to a user via an output unit.

The actual position of the accessory is the current position of the accessory that it occupies on the examination object and/or with respect to the examination object. The actual position may include a position in two dimensions or in three dimensions, as well as an orientation of the accessory on the examination object, in particular on the patient, and/or with respect to the examination object. Preferably, the acquisition unit is separate from the scanner of the magnetic resonance apparatus. For example, the acquisition unit may be a sensor and/or a camera. Alternatively, or in addition, the acquisition unit can be the scanner of the magnetic resonance apparatus. The actual position of the accessory may be acquired and/or determined in acquired magnetic resonance image data with the use of marking elements, which are arranged on the accessory. Alternatively, or in addition to the acquisition of the actual position with a sensor and/or a camera, the actual position of the accessory can be determined by a triangulation method. The actual position of the accessory is preferably determined with an accuracy of a few mm, as a maximum departure from the precise actual position.

The accessory may be a local radio-frequency antenna, which should be arranged directly surrounding the body area of the patient for examination for the acquisition of magnetic resonance signals. Alternatively, or in addition, the accessory may be an infusion unit and/or a positioning unit, such as a positioning pillow, and/or a respiration belt and/or further accessory items that appear expedient to those skilled in the art, which are required for a magnetic resonance examination.

The examination object is preferably a human or animal patient. Alternatively, the examination object may be a magnetic resonance phantom.

The target position is the ideal position of the accessory that the accessory should have for the pending magnetic resonance examination on the examination object, in particular on an area of the examination object for examination. The target position can be determined with the use of examination information of the patient. The examination information encompasses a body area of the patient for examination. The examination information can be stored in a database or entered by a user. In addition, the target position of the examination object can be determined with the use of acquired magnetic resonance image data of the examination object and/or with the use of acquired positioning data which is acquired by means of a camera. For example, the target position of the accessory can be determined by a recorded variable of the patient and/or a position of an area for examination of the examination object. In addition, the target position of the accessory can be recorded by a fixation state and/or fixation status of the accessory on a patient positioning device of the magnetic resonance scanner.

The determination unit preferably includes the magnetic resonance scanner. The determination unit may include a processor designed to determine the target position of the accessory. For the determination of the target position of the accessory the determination unit may also have or access software or computer programs stored in a memory or a data carrier, which contribute to the determination of the target position of the accessory during execution.

By operation of the determination unit, the actual position of the accessory can be compared with the target position of the accessory. For the comparison of the actual position of the accessory with the target position of the accessory, the determination unit may also have or access software or computer programs stored in a memory or a data carrier, which compare the actual position of the accessory with the target position of the accessory during execution. The deviation of the actual position of the accessory from the target position of the accessory is a difference between the actual position of the accessory and the target position of the accessory.

The output information may be an optical output information and/or acoustic output information. The output unit is preferably a component of the magnetic resonance scanner and/or the accessory, and may be an optical output unit, for example, a monitor and/or a display, and/or an acoustic output unit, for example, a speaker. The output unit can be arranged directly on the scanner of the magnetic resonance apparatus so that direct transmission of information to the user can be facilitated during the positioning of the accessory on the examination object. The output unit can be directly arranged on the accessory, whereby likewise the direct transmission of information to the user can be facilitated during the positioning of the accessory on the examination object. Preferably, the output information indicates to a user the extent of deviation of the actual position of the accessory from the target position. The user may be a medical technician supervising and/or preparing the pending magnetic resonance examination on the examination object. The output information can also indicate the target position of the accessory.

The invention has the advantage that an accessory such as a local radio-frequency antenna can be positioned on the examination object correctly by a less well-trained or an inexperienced member of staff, in particular on an area for examination of the examination object. Furthermore, the location and/or position and/or orientation of the accessory can also be individually optimized for the pending magnetic resonance examination on the examination object. This also means that high quality magnetic resonance image data can be recorded and/or acquired, and so highly relevant magnetic resonance image data can be provided. Unwanted repetitions of magnetic resonance examinations can be advantageously prevented in this manner.

In a further embodiment of the method according to the invention, the output information is first output information, and a correction of the actual position of the accessory is made by the determination unit, insofar as there is a deviation of the actual position of the accessory from the target position of the accessory. This is done by the determination unit generating the second output information representing the correction of the actual position of the accessory, and providing the second output information to the user via the output unit.

The second output information can also be provided to the user with the first output information in a single output step via the output unit.

Preferably, the position correction is detected or determined by the deviation determined between the actual position of the accessory and the target position of the accessory so that, when taking into account the position correction, the actual position of the accessory then coincides with the target position of the accessory. The second output information representing the position correction preferably includes an instruction for the user for the correct positioning of the accessory for the pending magnetic resonance examination. Such an instruction may be, for example, an instruction to turn and/or rotate and/or shift the accessory on the examination object.

According to the invention, the accessory can be a radio-frequency antenna placed contiguous to the examination object for the acquisition of magnetic resonance signals. The radio-frequency antenna is arranged around the area for examination of the examination object. For the acquisition of high quality image data, the correct position and/or orientation of such a local radio-frequency antenna on the examination object, in particular, the patient, is necessary. For example, a radio-frequency knee antenna can be used for a knee examination on the patient, and so is arranged around the knee of the patient for examination for this purpose. Local radio-frequency antennas, the position and/or orientation of which are often difficult for a user to adjust, can be advantageously positioned on the examination object with particular ease and speed.

When the acquisition of the actual position of the accessory is a sensor-based acquisition of the actual position of the accessory, the sensor-based acquisition of the actual position of the accessory can be implemented with the use of reference points of the examination object and/or with the use of reference points of the magnetic resonance scanner. The reference points also may be preferred physical features of the examination object, in particular, of the patient, such as articular points of the patient. The reference points may also be preferred positions and/or points of the magnetic resonance device such as an edge region of a patient receiving area and/or an edge region of a patient table of a patient positioning device. The reference points of the examination object and/or the reference points of the magnetic resonance scanner can also be provided by marking elements, so that there is a clear assignment of the respective reference points in the acquired images for recording the actual position of the accessory. Sensor-based acquisition preferably takes place by a sensor such as a camera, in particular, a 2-D camera or a 3-D camera. An advantage of this is that the easy and rapid acquisition of the actual position of the accessory can be provided to support the user.

In a further embodiment of the invention, the acquisition of the actual position of the accessory includes the acquisition of the orientation of the accessory in the examination room. The three-dimensional alignment and/or location of the accessory, for example, the three-dimensional alignment and/or location of a local radio-frequency antenna, can be advantageously recorded. This also enables a particularly accurate positioning and/or alignment of the accessory on the examination object.

Furthermore, the acquisition of the actual position of the accessory can include the acquisition of the fixation status of the accessory. The fixation status of the accessory represents a current fixation state of the accessory. For example, the fixation status of the accessory may include information as to whether the accessory is fixed, such as by a fixation unit, to the patient positioning device of the magnetic resonance scanner, or whether the accessory is not fixed. Preferably, the fixation unit has precisely defined fixation positions for this purpose, so that in the fixed state of the accessory, the actual position of the accessory can be concluded, and/or position information of the accessory can be provided to determine the actual position. The fixation status for a fixation position of the fixation unit can be detected electronically by a plug contact of the fixation unit. This enables position information already available regarding the position of the accessory to be used to determine the actual position of the accessory.

Furthermore, the determination of the target position of the accessory can include the determination of an examination region of the examination object. The examination region of the examination object is an area for examination of the examination object. An individual target position of the accessory tailored to the examination object, in particular, to the position and/or location of the examination region, can be determined. Advantageously, anatomical properties of the examination object, in particular, of a patient, can also be taken into account in this way when ascertaining and/or determining the target position of the accessory. For example, an absolute position of an organ for examination with regard to a reference point of the magnetic resonance device can depend on a variable of the patient.

Furthermore, the determination of the target position of the accessory can be a determination using an overview measurement of the examination object. The overview measurement, in particular, a localizer scan, is preferably performed on the patient before the pending magnetic resonance examination, in order to plan the pending magnetic resonance examination with the use of the overview measurement. The overview measurement, in particular, the localizer measurement, is preferably acquired in the image data with a lower resolution than a resolution from image data of the pending magnetic resonance examination. Preferably, the overview measurement comprises image data from the area for examination of the examination object such as, for example, an organ area of the patient for examination. In addition, the overview measurement may also comprise image data from the entire examination object such as, for example, the entire patient. Hereby, data for ascertaining and/or determining the target position of the accessory can be advantageously provided in a particularly time-saving manner with the use of overview data already in existence and/or to be acquired. Additional measurements for the acquisition of data to ascertain and/or determine the target position of the accessory can also be dispensed with advantageously in this manner.

In an embodiment of the invention, a model of the examination object is created in order to determine the target position of the accessory. The model preferably is an artificially generated image or an artificially generated figure, for example, a graphic figure and/or a 3-D figure that represents the examination object in virtual environments, such as an avatar. Preferably, the model is created and/or generated by the determination unit or a further unit, wherein acquired data of an overview measurement may form the basis of determination such that the model and the examination object coincide as far as possible. Alternatively, or in addition, the model can be created or generated with the use of existing image data of the examination object and/or also with the use of camera data. To determine or ascertain the model, the model can be adapted to the image data or the overview data and/or the camera data. To this end, the determination unit or the additional unit may include and/or access software and/or computer programs that are stored in a memory and/or a data carrier, and which generate the model of the examination object during execution. This embodiment of the invention has the advantage that the position of the accessory can be individually adapted or optimized to suit the examination object, for example, to anatomical properties of the examination object. This also enables less well-trained medical operating personnel to position the accessory on the examination object with ease.

In another embodiment, the output information includes positioning information for the target position of the accessory, so a representation of the target position is provided for the medical operating personnel, for the positioning of the accessory. The user can immediately recognize the correct position of the accessory with the use of the positioning information that is presented.

In another embodiment of the invention, further output information is generated as soon as the actual position of the accessory coincides with the target position of the accessory. This has the advantage that the user receives direct feedback or is directly informed as soon as the actual position of the accessory coincides with the target position of the accessory.

Preferably, the additional output information is emitted immediately after the generation of the additional output information via the output unit. Preferably, the additional output information may include an instruction to the user, such as that the accessory can and/or should be fastened in the current position, which is preferably the target position of the accessory. The additional output information may also only include illumination of an indicator light that indicates to the user that the accessory is situated in its target position. Time-saving and simple positioning of the accessory on the examination object can be achieved thereby.

Furthermore, the invention concerns a magnetic resonance apparatus with a scanner, an acquisition unit that acquires an actual position of an accessory, a determination unit that determines a target position of the accessory, an output unit, and the accessory. The magnetic resonance apparatus is designed to operate the magnetic apparatus so as to perform the method according to the invention as described above.

The magnetic resonance apparatus is designed in this way has the advantage that an accessory such as a local radio-frequency antenna, can be positioned correctly on the examination object by less well-trained or inexperienced personnel, in particular, on an area for examination of the examination object, for example, a patient. Furthermore, a location and/or position and/or orientation of the accessory can also be individually optimized for the pending magnetic resonance examination on the examination object (the patient). This also allows high quality magnetic resonance image data to be reconstructed from the high quality magnetic resonance raw data thus acquired. Undesirable repetitions of magnetic resonance examinations are advantageously avoided in this way.

The advantages of the magnetic resonance apparatus according to the invention essentially correspond to the advantages of the method according to the invention, as described in detail above. Features and alternative embodiments mentioned above are likewise applicable to the apparatus.

In an embodiment of the magnetic resonance apparatus, the acquisition unit is a sensor. This enables simple and direct acquisition of the actual position of the accessory, in particular, the current, actual position of the accessory, on the examination object. The sensor may be a camera such as a 2-D camera or a 3-D camera. The camera is preferably arranged such that a preparation area for preparation of the examination object (the patient) is situated in an acquisition area (field of view) of the camera. Preferably, the examination object is lying on a patient positioning device immediately in front of the magnetic resonance scanner.

Alternatively or in addition, the sensor may be or include a rotation sensor. This enables a particularly accurate acquisition of the orientation and/or alignment of the accessory on the examination object. The rotation sensor is preferably situated on the accessory and/or inside the accessory, such that the orientation and/or location of the accessory can be directly acquired. The rotation sensor may be a gyroscope sensor such as an acceleration sensor and/or a position sensor, which responds to even slight accelerations and/or rotations and/or position changes affecting the gyroscope sensor. The principle of the gyroscope sensor is based on mass inertia. The rotations and/or position changes acquired from a gyroscope sensor are detected and emitted in the form of an electrical signal representing a change in voltage dependent on the rotation speed, which is evaluated by the determination unit (processor).

Furthermore, the acquisition unit can include a fixation unit. Such a fixation unit provides position information with which the current fixation status and/or current fixation state of the accessory can be ascertained, for determining the actual position of the accessory. The fixation unit can be at least partially integrated in the accessory, such as a plug contact integrated in a local radio-frequency antenna that, during positioning of the local radio-frequency antenna is plugged into a mating socket at the patient positioning device of the magnetic resonance scanner.

In an embodiment of the invention, the accessory is a radio-frequency antenna for the acquisition of magnetic resonance signals contiguous to the examination object. The position and/or orientation of such local antennas are often difficult for a user to adjust, but the invention allows such a local antenna to be positioned on the examination object with particular ease and speed. To acquire high quality image data, a correct position and/or orientation of a local radio-frequency antenna on the examination object, in particular, the patient, is necessary so that high quality raw data can be acquired. Accurate positioning of an accessory such as a local radio-frequency antenna is achieved with the method according to the invention.

In a further embodiment, the output unit is stated on the scanner or on the accessory. Thus, during preparation of the examination object, in particular positioning of the accessory on the patient, output information, in particular, the first output information or the first output information together with further output information, can be provided directly to the user. The output unit may be an optical output unit and/or an acoustic output unit. For example, the output unit may have a display and/or LEDs arranged directly on the accessory.

The present invention also encompasses a non-transitory, computer-readable data storage medium encoded with programming instructions that, when the storage medium is loaded into a computer or computer system of a magnetic resonance apparatus, cause the computer or computer system to operate the magnetic resonance apparatus in order to implement any or all embodiments of the method according to the invention, as described above.

The program code may require program resources, e.g. libraries and auxiliary functions, to realize the corresponding embodiments of the method. The program code may be a source code, which has still to be compiled and linked or only interpreted, or an executable software code which only remains to be loaded into a corresponding arithmetic unit for execution.

BRIEF DESCRIPTION OF THE DRAWINGS

FIG. 2 is a flowchart of the method according to the invention for supporting a user when positioning an accessory for a magnetic resonance examination on an examination object.

DESCRIPTION OF THE PREFERRED EMBODIMENTS

Figure 1:
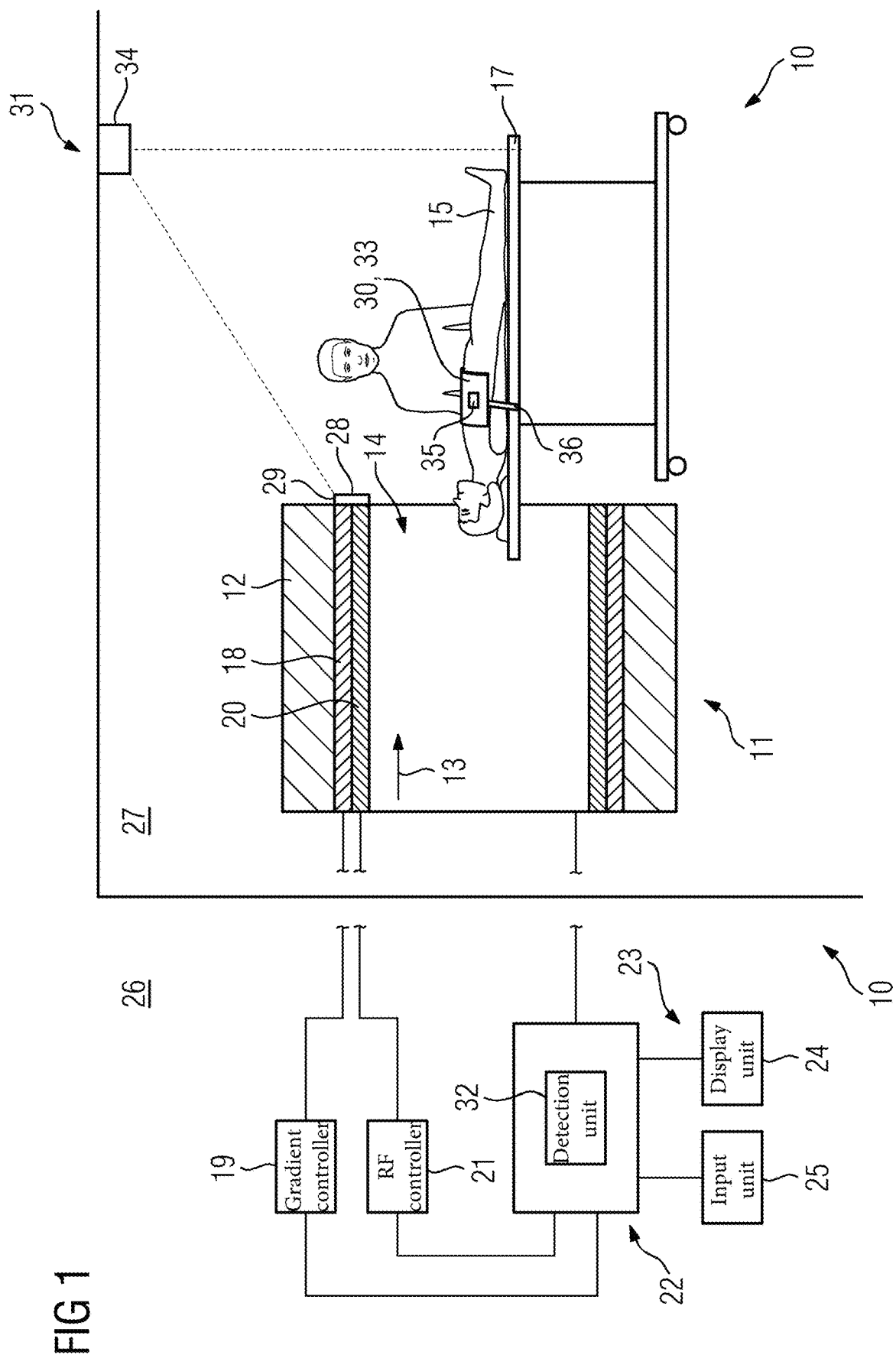
FIG. 1 schematically illustrates a magnetic resonance apparatus according to the invention.

FIG. 1 shows a magnetic resonance apparatus 10 having a scanner 11, which has a superconducting basic field magnet 12 that generates a strong and constant basic magnetic field 13. The scanner 11 has a patient receiving area 14 for recording an examination object 15, in particular, a patient. The patient receiving area 14 in the exemplary embodiment is cylindrical in design, and is circumferentially surrounded by the scanner 11. In principle, however, embodiments of the patient receiving area 14 that deviate from this tunnel are feasible. The examination object 15 can be moved or driven into the patient receiving area 14 by a patient positioning device 16. The patient positioning device 16 has a patient table 17 that is movable inside the patient receiving area 14.

Furthermore, the scanner 11 has a gradient coil arrangement 18 that generates magnetic field gradients for spatially encoding magnetic resonance signals during imaging. The gradient coil arrangement 18 is controlled by a gradient controller 19 of the magnetic resonance apparatus 10. The scanner 11 also has a radio-frequency (RF) antenna 20 that is controlled by an RF controller 21 so as to radiate a radio-frequency sequence into the patient receiving area 14. The radiated radio-frequency sequence causes certain nuclear spins in the examination object 15 to be deflected from previous alignment with the basic magnetic field 13, by an amount known as a flip angle. As the excited nuclear spins relax and return to the steady state, they emit radio-frequency signals, which are the aforementioned magnetic resonance signals. The magnetic resonance signals are detected by the same RF antenna 20 from which the radio-frequency sequence was radiated, or by a different RF reception antenna, such as a local coil, serving as an accessory 30.

The magnetic resonance apparatus 10 has a control computer 22 that controls the basic field magnet 12, the gradient controller 19 and the RF controller 21. The control computer 22 centrally controls the magnetic resonance apparatus 10 such as perform a predetermined gradient echo sequence. In addition, the control computer 22 has an evaluation processor for evaluation of the raw data acquired during the magnetic resonance examination, such as for reconstructing image data therefrom. The control computer 22 has and/or can access software and/or computer programs that are executed by the control computer 22. The software and/or computer program is designed so that the basic field magnet, the gradient controller 19 and the RF controller 21 are controlled during the execution of the software and/or computer programs. In addition, the control computer may have and/or access software and/or computer programs designed to control and/or perform a magnetic resonance examination by operation of the magnetic resonance apparatus.

Furthermore, the magnetic resonance apparatus 10 has a first user interface 23 that is linked to the control computer 22. Control information such as imaging parameters, and reconstructed magnetic resonance images can be displayed on a display unit 24, for example, on at least one monitor, of the first user interface 23, for medical operating personnel. Furthermore, the first user interface 23 has an input unit 25 via which information and/or parameters can be entered by the medical operating personnel during a measurement process. The first user interface 23 is arranged inside a control room 26, and the control computer 22 is also arranged inside the control room 26.

The scanner 11 is arranged inside an examination room 27. The examination room 27 is separated from the control room 26. The examination room 27 is preferably shielded outwardly and inwardly against disturbing influences that can influence a magnetic resonance examination as well as be caused by the scanner 11. For example, the examination room 27 is shielded with regard to magnetic fields as well as from electromagnetic radiation, in particular, radio-frequency radiation.

The magnetic resonance apparatus 10 has a second user interface 28 with an output unit 29. The second user interface 28 is arranged inside the examination room 27. In the exemplary embodiment, the output unit 29 is an optical output unit with a display, which is arranged directly on the scanner 11. It may also be the case that the output unit 29 is arranged directly on an accessory 30 such as a local radio-frequency antenna. The display is preferably detachable from the scanner 11. The display may also be formed as a touch display. Alternatively, the output unit 29 may also have directional LED elements, which can be arranged directly on the accessory 30, in particular, the local radio-frequency antenna. The output unit 29 may be or, also have an acoustic output unit.

Furthermore, the magnetic resonance apparatus 10 has an acquisition unit 31, a determination unit 32 and the accessory 30. In the present exemplary embodiment, the accessory 30 is formed as a local radio-frequency antenna 33. During the magnetic resonance examination, magnetic resonance signals are detected by the local radio-frequency antenna 33. To this end, the local radio-frequency antenna 33 is placed on the area for examination of the examination object 15, in particular, the patient. The accessory 30, the local radio-frequency antenna 33, is preferably put in place manually by the user (the medical operating personnel).

In a further embodiment of the invention the accessory 30 may be a positioning element for positioning of the examination object 15, an infusion unit and/or further accessory unit considered reasonable to those skilled in the art.

The acquisition unit 31 of the magnetic resonance apparatus 10 is designed to record the actual position of the accessory 30. The acquisition unit 31 is arranged inside the examination room 27. The acquisition unit 31 has a sensor 34. In the exemplary embodiment, the sensor 34 is a camera. The camera may be a 2-D camera. Preferably, however, the camera is a 3-D camera. To detect the actual position of the accessory 30, the camera is arranged in the examination room 27 such that the patient positioning device 16, together with the examination object 15, is within an acquisition area (field of view) of the camera during the preparation of a magnetic resonance examination. For example, the camera can be arranged on a ceiling of the examination room 27 for this purpose.

Furthermore, the acquisition unit 31 has a rotation sensor 35. In the exemplary embodiment, the rotation sensor 35 is a gyroscope sensor, which is arranged on the accessory 30 or inside the accessory 30. In addition, the acquisition unit 31 can have a fixation unit 36 that affixes the accessory 30 to the patient positioning device 16.

FIG. 2 shows the basic steps of the method according to the invention for supporting a user when positioning the accessory 30 for a magnetic resonance examination on an examination object 15. The method is controlled by the determination unit 32 so that the method is performed automatically by the determination unit 32, together with the output unit 29. The acquisition unit 31 has the necessary software and/or computer programs for this purpose or can access this necessary software and/or computer programs. The software and/or computer programs are stored in a memory or a non-transitory, electronically readable data storage medium. During execution of the software and/or computer programs by means of a processor of the determination unit 32, the software and/or computer programs perform the method for supporting a user when positioning an accessory 30 for a magnetic resonance examination on an examination object 15. The memory may be a component of the determination unit 32. The memory may be an external data carrier that can be loaded into the determination unit 32 or the computer 22.

The examination object 15 is arranged on the patient positioning device 15, in particular on the movable patient table 16, at the start of the method. The movable patient table 16 with the examination object 15 thereon are located inside the examination room 27. The movable patient table 17 is inside the acquisition area of the acquisition unit 31. The examination object 15 thus is arranged inside the acquisition area of the acquisition unit 31. In the exemplary embodiment, as noted the examination object 15 is a patient. The examination object 15 may alternatively be a phantom.

First, the accessory 30 is placed on the patient by the user, in particular, medical operating personnel supervising the magnetic resonance examination. In a step 100, the actual position of the accessory 30, (i.e., the current position of the accessory 30 on the patient) is acquired by the acquisition unit 31.

The actual position can be acquired by the sensor 34, in particular, the camera in the sensor-based acquisition of the actual position of the accessory 30. A 2-D position of the accessory 30, hence a position of the accessory 30 in two dimensions, is preferably acquired by the camera when the camera is a 2-D camera. More preferably, however, a 3-D position of the accessory 30, hence a position of the accessory 30 in three dimensions, is acquired by the camera when the camera is a 3-D camera.

Preferably, the sensor-based acquisition of the actual position of the accessory 30 takes place with respect to reference points. The reference points may be reference points on the examination object 15. For example, the reference points may be articular points of a patient. Alternatively, or in addition, the reference points may be reference points on the magnetic resonance apparatus 10, such as reference points on the movable patient table 17 or reference points in an opening area of the patient receiving area 14 of the scanner 11. The position of the accessory 30 with respect to these reference points can therefore be acquired by the camera serving as the sensor 34.

The actual position of the accessory 30 also can be acquired by a triangulation method. The camera data of the camera serving as the sensor 34 can also be used to acquire the actual position of the accessory 30. In order to determine the actual position of the accessory 30 by such a triangulation method, the acquisition unit 31 may also have software and/or computer programs designed to determine the actual position of the accessory 30 by the triangulation method. In addition, the actual position of the accessory 30 by triangulation can be implemented with the use of camera data from the determination unit 32. Alternatively or in addition, the determination unit 32 may have software and/or computer programs designed to determine the actual position of the accessory 30 by triangulation with the use of camera data of the camera serving as the sensor 34.

In addition, the actual position can be acquired by the rotation sensor 35. The orientation and/or location and/or alignment of the accessory 30 is acquired in the room by the rotation sensor 35. The rotation sensor 35 may be, for example, a gyroscope sensor that acquires the orientation and/or location and/or alignment of the accessory 30.

Furthermore, the actual position of the accessory 30 can be acquired by the fixation unit 36. For example, a fixation state of the accessory 30 can be determined by the fixation unit 36. The fixation state can be detected by the camera serving as the sensor 34, for example, with the use of a location and/or position of fixing belts of the fixation unit 36.

Furthermore, the fixation state can also be determined with the use of fixation elements arranged directly on the local radio-frequency antenna 33, for example, by determining a fixation status and/or a fixation state of the accessory 30 according to the plug state of the fixation element of the local radio-frequency antenna 33.

In an embodiment, the actual state of the accessory 30 is acquired only by the sensor-based acquisition of the actual position with the use of reference points. In another embodiment, the actual state of the accessory 30 is acquired only by the acquisition of the orientation of the accessory 30 in the room. In another embodiment, the actual state of the accessory 30 is acquired only by the acquisition of the fixation status of the accessory 30. In another embodiment, the actual position of the accessory 30 is acquired only by the combination of the sensor-based acquisition of the actual position with the use of reference points and the orientation of the accessory 30 in the room and the fixation status of the accessory 30.

In a further step 101, a target position of the accessory 30 is determined by the determination unit 32. To ascertain the target position of the accessory 30, an examination region of the examination object 15, in particular, the patient, is determined by the determination unit 32. For example, this can be done with the use of examination information and/or patient information. The examination information and/or the patient information can be stored inside the control computer 22 and retrieved by the determination unit 32. In addition, the examination information and/or the patient information can also be stored in a hospital information system (HIS) and/or in a radiology information system (RIS) and retrieved by the determination unit 32.

Furthermore, to determine the target position of the accessory 30, image data of an overview measurement and/or a localizer measurement of the patient are made available. Preferably, the overview measurement and/or localizer measurement are performed by the scanner 11 of the magnetic resonance apparatus 10. Based on the image data of the overview measurement, a model of the patient can be created by the determination unit 32. Preferably, the model is matched to the image data of the overview measurement and/or the localizer measurement by the determination unit 32. With the model that, for example, can also be an avatar of the examination object 15 (the patient), the examination region of the patient and thus the target position of the accessory 30, such as, for example, a lung region of the patient, can be concluded very precisely.

Insofar as the target position of the accessory 30 has already been determined and is available due to a previous sequence of the method for supporting the user when positioning the accessory 30 for a magnetic resonance examination on the examination object 15, the determination of the target position of the accessory 30 may also involve retrieving the target position of the accessory 30 that was already determined.

In a further subsequent step 102, the actual position of the accessory 30 is compared with the target position of the accessory 30 with regard to a deviation of the actual position of the accessory 30 from the target position of the accessory 30. The deviation between the actual position of the accessory 30 and the target position of the accessory 30 takes place both with regard to a position of the accessory 30 as well as with regard to an orientation and/or location and/or alignment of the accessory 30. The actual position of the accessory 30 is compared with the target position of the accessory 30 by the determination unit 32.

In a further step 103, first output information is generated by the determination unit 32 as a result of the comparison of the actual position of the accessory 30 with the target position of the accessory 30. The first output information contains information for the user as to how well the actual position of the accessory 30 coincides with the target position of the accessory 30. In addition, the first output information may also include position information regarding the target position of the accessory 30.

In a further step 104, the first output information is provided to the user via the output unit 29 of the second user interface 28.

Insofar as the actual position of the accessory 30 coincides with the target position of the accessory 30, further output information can be generated. This further output information may include, for example, a request to the user to fasten the accessory 30, in particular, the local radio-frequency antenna 33. The further output information can then likewise be provided by the output unit 29.

Insofar as the actual position of the accessory 30 deviates from the target position of the accessory 30, a correction of the actual position of the accessory 30 is determined by the determination unit 32 in a further step 105. The position correction of the actual position preferably comprises a correction value such that the actual position of the accessory 30 coincides with the target position of the accessory 30, taking the correction value into account. With the use of the position correction of the actual position of the accessory 30, in a further step 106, second output information is generated that includes the position correction of the actual position of the accessory 30. The second output information preferably includes a suggested correction for the accessory 30 to the user. In a further step 107, the output information is provided to the user via the second user interface 28, in particular, the output unit 29 of the user interface 28.

Then in a further step 108, the accessory 30, in particular, the local radio-frequency antenna 33, is positioned on the patient.

As soon as the accessory 30 has been repositioned, a renewed acquisition of the actual position of the accessory 30 takes place and the steps 100 to 104 are performed again automatically by the determination unit 32. Only when the actual position of the accessory 30 coincides with the target position of the accessory 30 is this indicated to the user via the output unit 29 and the further output information in the step 104.

As soon as the accessory 30, in particular, the local radio-frequency antenna 33, is arranged in the correct position with the correct orientation and/or location, this is recognized during the performance of the method according to the invention in the step 102, and in the steps 103 and 104 corresponding output information is generated and output to the user. In addition, in a further, optional step 110, further output information can be generated by the determination unit 32. This further output information may include, for example, a request to fasten the accessory 30, in particular, the local radio-frequency coil unit 33, in the current actual position of the accessory 30. Then, in a further step 111, this further output information can be provided to the user, in particular, to the medical operating personnel, via the output unit 29 of the second user interface 28. In addition, in an optional step 109, the magnetic resonance examination can be started on the patient.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for supporting a user when positioning an accessory, for conducting a magnetic resonance (MR) examination of an examination object in an MR scanner, said method comprising:
    operating sensor circuitry in order to acquire an actual position of the accessory in the MR scanner;
    operating the MR scanner to perform an overview measurement of the examination subject;
    generating, from the overview measurement, an artificial image that comprises a three-dimensional (3D) model of the examination subject having physical features matching that of the examination object;
    operating processor circuitry in order to determine a target position of the accessory from the model of the examination object provided to said processor circuitry;
    in the processor circuitry, comparing the actual position of the accessory with the target position of the accessory in order to identify a deviation of the actual position of the accessory from the target position of the accessory; and
    providing output information to the user that represents said deviation, via an output.

2. A method as claimed in claim 1 comprising:
    in said processor circuitry, when a deviation of the actual position of the accessory from the target position of the accessory exists, determining, in said processor circuitry, a position correction of the accessory that is needed in order to remove said deviation;
    in said processor circuitry, generating further output information that represents said position correction; and
    providing said additional output information to the user via said output.

3. A method as claimed in claim 1 wherein said accessory is a radio-frequency antenna placeable on the examination object in order to acquire MR signals from the examination object.

4. A method as claimed in claim 1 wherein said sensor circuitry comprises a camera configured to acquire the actual position of the accessory, with respect to reference points selected from the group consisting of reference points of the examination object and reference points of the MR scanner.

5. A method as claimed in claim 1 comprising operating said sensor circuitry to acquire the actual position of the accessory by acquiring an orientation of the accessory in a room in which the MR scanner is situated.

6. A method as claimed in claim 1 comprising operating the sensor circuitry to acquire the actual position of the accessory by acquiring a fixation status of the accessory.

7. A method as claimed in claim 1 comprising determining said target position of the accessory as a determination of an examination region of the examination object.

8. A method as claimed in claim 1 comprising determining the target position of the accessory by implementing an overview measurement of the examination object with said MR scanner.

9. A method as claimed in claim 1 comprising generating said output information so as to represent positioning information for achieving said target position with the accessory.

10. A method as claimed in claim 1 comprising, as soon as said actual position of the accessory coincides with said target position of the accessory, providing further output information via said output that indicates that the coincidence has been achieved.

11. A method as claimed in claim 1 wherein the model is an avatar.

12. A magnetic resonance (MR) apparatus comprising:
    an MR scanner;
    an accessory that is positionable with respect to an examination object in said MR scanner;
    sensor circuitry configured to acquire an actual position of the accessory;
    processor circuitry configured to:
        perform an overview measurement of the examination subject;
        generate, from the overview measurement, an artificial image that comprises a three-dimensional (3D) model of the examination subject having physical features matching that of the examination object;
        determine a target position of the accessory from the model of the examination object provided to said processor circuitry; and
        compare the actual position of the accessory with said target position of the accessory in order to determine a deviation of the actual position of the accessory from said target position of the accessory, and configured to generate output information that represents said deviation; and
    an output configured to be in communication with said processor circuitry at which said output information is presented to a user.

13. An MR apparatus as claimed in claim 12 wherein the model is an avatar.

14. A non-transitory, computer-readable data storage medium encoded with programming instructions, said storage medium being loaded into a computer system of a magnetic resonance (MR) apparatus that comprises an MR scanner used with an accessory, said programming instructions causing said computer system to:
    operate sensor circuitry in order to acquire an actual position of the accessory in the MR scanner;
    operate the MR scanner to perform an overview measurement of the examination subject;
    generate, from the overview measurement, an artificial image that comprises a three-dimensional (3D) model of the examination subject having physical features matching that of the examination object;
    operate processor circuitry in order to determine a target position of the accessory from the model of the examination object provided to said processor circuitry;
    compare the actual position of the accessory with the target position of the accessory in order to identify a deviation of the actual position of the accessory from the target position of the accessory; and
    provide output information to the user that represents said deviation, via an output.

* * * * *